(12) United States Patent
Staunton et al.

(10) Patent No.: US 7,267,669 B2
(45) Date of Patent: Sep. 11, 2007

(54) TWO SITE INFUSION APPARATUS

(75) Inventors: Doug Staunton, Kalamazoo, MI (US); Jason Toman, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 259 days.

(21) Appl. No.: 10/765,516

(22) Filed: Jan. 26, 2004

(65) Prior Publication Data

US 2004/0158210 A1 Aug. 12, 2004

Related U.S. Application Data

(63) Continuation of application No. 10/461,939, filed on Jun. 13, 2003, which is a continuation-in-part of application No. 10/083,266, filed on Feb. 23, 2002, now Pat. No. 6,679,862.

(60) Provisional application No. 60/451,161, filed on Feb. 28, 2003.

(51) Int. Cl.
*A61M 5/00* (2006.01)

(52) U.S. Cl. ............... 604/247; 604/173; 251/331; 137/512.4

(58) Field of Classification Search ........ 604/246–249, 604/256, 31, 33, 151, 153, 131, 236–7, 141, 604/505, 94.01, 284, 533–539, 258, 173; 137/510, 883, 512.4; 251/45, 331
See application file for complete search history.

(56) References Cited

U.S. PATENT DOCUMENTS

| 1,871,535 | A | * | 8/1932 | Lattner | .................. | 137/115.14 |
|---|---|---|---|---|---|---|
| 2,926,683 | A | * | 3/1960 | Windsor et al. | ............ | 137/510 |
| 4,276,237 | A | * | 6/1981 | Barker et al. | .............. | 261/39.2 |
| 4,874,386 | A | * | 10/1989 | O'Boyle | ..................... | 604/246 |
| 5,213,468 | A | * | 5/1993 | Sexton et al. | ............ | 415/121.3 |
| 5,287,841 | A | * | 2/1994 | Forsythe et al. | ............ | 123/510 |
| 6,251,098 | B1 | * | 6/2001 | Rake et al. | ................. | 604/408 |
| 6,341,760 | B1 | * | 1/2002 | Rawlings | .................... | 251/207 |
| 6,378,542 | B1 | * | 4/2002 | DuHack | ........................ | 137/8 |
| 6,460,367 | B1 | * | 10/2002 | DuHack | ...................... | 62/337 |

* cited by examiner

*Primary Examiner*—Kevin C. Sirmons
*Assistant Examiner*—Andrew Gilbert
(74) *Attorney, Agent, or Firm*—Howard & Howard Attorneys, P.C.

(57) ABSTRACT

An apparatus for use in delivering pain medication to separate locations from a single source of pressurized medication includes a valve housing, a cap, and a flexible diaphragm. The valve housing includes a first end and a second end and an inlet passage. The first end includes first and second outlet orifices. The cap has a closed end and an open end and is removably coupled to the valve housing at the open end. The flexible diaphragm is coupled between the cap and the valve housing and is movable from a closed position to an open position. The flexible diaphragm seals a pressure chamber from the first and second outlet orifices when in the closed position and opens the first and second outlet orifices to the pressure chamber when in the open position.

23 Claims, 9 Drawing Sheets

TWO SITE INFUSION APPARATUS

This application claims priority to U.S. Provisional Application Ser. No. 60/451,161, filed Feb. 28, 2003, and is a continuation of U.S. patent application Ser. No. 10/461,939, filed Jun. 13, 2003, which is a Continuation in Part of U.S. patent application Ser. No. 10/083,266, filed Feb. 23, 2002, now U.S. Pat. No. 6,679,862.

TECHNICAL FIELD

The present invention relates generally to the delivery of a pulsatile fluid pulse, and more particularly, to an apparatus for controllably dividing a pulsatile fluid flow into two or more pulsatile fluid flows.

BACKGROUND OF THE INVENTION

It is sometimes desirable to deliver a fluid using a pulsatile fluid flow or series of pulses. For example, some medication delivery systems which utilize a series of pulsatile fluid pulses to deliver medication, are known in the art. Medication delivery systems may be used to deliver pain control medication and other medications intraoperatively or post-operatively, subcutaneously, and percutaneously to a patient after a surgical, or some other medical, procedure.

For example, U.S. Pat. No. 5,807,075 to Jacobsen et al. discloses a conventional medication delivery system that includes a base housing and a cassette. The base housing of the '075 patent houses electronic components, such as an electric motor, a power source, and an electronic controller, and the cassette of the '075 patent interacts with a supply of the medication to deliver the medication to the patient.

A further example of a conventional medication delivery system is disclosed in U.S. Pat. No. 4,650,469 to Berg et al. This patent discloses a medication delivery system that includes a control module and a reservoir module removably connected to the control module. The control module includes a pump mechanism, valves, a power source, electronic controls, and the like, and the reservoir module includes a container that supplies the medication to be delivered to the patient.

It is known to use an electric motor in such medication delivery systems, where each revolution or cycle of the motor delivers a preset amount of medication. Such systems are known as positive displacement systems. In such systems, the flow of medication is not pressurized unless it meets a restriction.

Generally, conventional medication delivery systems provide a flow of medication through an output tube which then is delivered to the patient, as required. However in some procedures, medication is required at two locations with respect to the patient, for example, breast augmentation or reconstruction. Another such procedure where medication delivery is desirable at two sites is an autologous graft procedure where it is desirable to deliver medication at both the graft and the donor sites. If the medication provided by the delivery system is pumped through a "Y" connection, then the medication will not be delivered to each site or location evenly for several reasons. First, unequal pressure at the two infusion sites due to elevation or intracompartmental pressure sets up a siphon where flow occurs from the higher pressure side to the lower pressure side in the period between pulses. Furthermore, if the flow of medication on one side of the "Y" has a greater restriction than on the other side, back pressure may reduce or stop the flow of medication on that side. This is undesirable.

One solution would be to provide a check valve in each leg after the "Y" connection. This solution presents several problems, namely, there is a time delay added by the opening and closing of the check valve and differences in manufacturing tolerances contributing to the delay may also lead to uneven delivery of the medication. Furthermore, most check valves restrict flow when open, and unequal or uncontrollable variations in this restriction would lead to unequal flow.

Another solution would be to provide a large fluid resistor (small orifice) in each leg. Correctly sizing this orifice would cause the pressure to rise substantially higher than the downstream pressure differences. This pressure could be driven up over several pulses. If the pressure remained higher than the highest downstream pressure, no backflow due to siphoning could occur. Furthermore, the difference in the pressure drop in the two downstream legs could be controlled to remain relatively equal. This solution presents several problems. First, the maximum pressure reached to provide the necessary flow split accuracy can be very high. This can interfere with other pump features such as an occlusion alarm, and can cause sealing difficulties. Second, if the pump has a user selectable flow rate, the size of the glass orifice must be fixed to work with the lowest possible flow rate. This aggravates the maximum pressure problem should the pump be used at its highest flow rates.

The present invention is aimed at one or more of the problems set forth above.

SUMMARY OF THE INVENTION AND ADVANTAGES

In one aspect of the present invention, an apparatus for use in delivering pain medication to separate locations from a single source of pressurized medication is provided. The apparatus includes a valve housing, a cap, and a flexible diaphragm. The valve housing includes a first end and a second end and an inlet passage. The first end includes first and second outlet orifices. The cap has a closed end and an open end and is removably coupled to the valve housing at the open end. The flexible diaphragm is coupled between the cap and the valve housing and is movable from a closed position to an open position. The flexible diaphragm seals a pressure chamber from the first and second outlet orifices when in the closed position and opens the first and second outlet orifices to the pressure chamber when in the open position.

In another aspect of the present invention, an apparatus for use in delivering pain medication to separate locations from a single pulsatile flow of medication, is provided. The apparatus includes a valve housing having a first end and a second end. The first end includes first and second outlet orifices. The second end forms a pressure chamber. The valve housing further includes an inlet orifice coupled to the pressure chamber by an inlet passage. The first and second outlet orifices are coupled to the pressure chamber by first and second outlet passages, respectively. A cap has a closed end and an open end and is removably coupled to the valve housing at the open end. A flexible diaphragm is coupled between the cap and the valve housing and is movable from a closed position to an open position, the flexible diaphragm sealing the pressure chamber from the first and second outlet orifices when in the closed position and opening the first and second outlet orifices to the pressure chamber when in the open position. The second end of the valve housing and the flexible diaphragm form a pressure chamber. The valve housing further includes an inlet orifice coupled to the pressure chamber by an inlet passage. The first and second outlet orifices are coupled to the pressure chamber by first and second outlet passages, respectively.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

With reference to the drawings and in operation, the present invention provides an apparatus 10 for use in delivering pain medication to separate locations from a single pulsatile source of medication (or two site infusion apparatus). In one embodiment, the source of medication is a medication delivery system which includes a positive displacement pump (not shown). For example, the medication delivery system could include an electrical motor. The system is designed to deliver through a tube or inlet tube 12 a preset amount of medication every revolution or cycle of the motor. The rate at which medication is delivered may be set by varying the time between cycles of the motor.

In one aspect of the present invention, the two site infusion apparatus 10 is coupled to the output tube 12. The two site infusion apparatus 10, as discussed below, splits the medication delivered from the delivery system and delivers the medicine through first and second outlet orifices 14A, 14B.

The apparatus 10 includes a valve housing 16. The valve housing 16 includes a first end 18 and a second end 20. The first end 18 includes the first and second outlet orifices 14A, 14B.

An end cap 30 has a closed end 32 and an open end 34. The end cap 30 is removably coupled to the valve housing 16 at the open end 34. A flexible diaphragm 36 is coupled between the end cap 30 and the valve housing 16 and is movable from a closed position to and an open position by the fluid energy of the pulse. The second end 20 of the valve housing 16 and the flexible diaphragm 36 form a pressure chamber 22. The valve housing 16 further includes an inlet orifice 24. The inlet orifice 24 is coupled to the pressure chamber 22 by an inlet passage 26. The first and second outlet orifices 14A, 14B are coupled to the pressure chamber 22 by first and second outlet passages 28A, 28B, respectively. The flexible diaphragm 36 seals the pressure chamber 22 from the first and second outlet orifices 28A, 28B when the flexible diaphragm 36 is in the closed position and opens the first and second outlet orifices 28A, 28B to the pressure chamber 22 when the flexible diaphragm 36 is in the open position.

The valve housing 16 also includes a routing passageway 38 adjacent the inlet passage 26. The routing passageway 38 allows the medication delivery system inlet tube 12 to be secured within the valve housing 16. In one embodiment of the present invention, the end of the inlet tube 12 coated with a solvent and inserted through the inlet passage to the inlet orifice 24. The inlet orifice 24 and the output tube 12 have an interference fit. The solvent bonds the inlet tube 12 and the inlet orifice 24.

As shown, in one embodiment of the present invention, the open end 34 of the cap 30 has an outer perimeter 38. The outer perimeter 38 includes a ridge 40. The second end 20 of the valve housing 16 includes a detent 42 along its outer perimeter 44. The detent 42 receives the ridge 40 which allows the valve housing 16 and the end cap 30 to be removably snapped together.

In another aspect of the present invention, the apparatus 10 includes a biasing mechanism 44 coupled between the cap 30 and the flexible diaphragm 36 for biasing the flexible diaphragm 36 towards the closed position. In one embodiment of the present invention, the biasing mechanism 44 includes a biasing spring 46. The biasing spring 46 may be either tubular or conical.

In another aspect of the present invention, a piston 48 may be juxtaposed between the biasing spring 46 and the flexible diaphragm 36. In one embodiment, the flexible diaphragm 36 includes a piston receiving aperture 50 for receiving a first end 52 of the piston 48.

As shown, in one embodiment, the piston 48 is hollow and includes a spring receiving chamber 54. The end cap 30 includes a spring positioning pin 56. One end of the spring 46 is seated within the spring receiving chamber 54 and the other end is centered on the spring position pin 56.

In another aspect of the present invention, the apparatus 10 includes first and second bushings 58A, 58B which are located within and have an interference fit with the first and second outlet orifices 14A,14B. First and second flow restricting components 60A, 60B are positioned within and have an interference fit with the first and second bushings 58A, 58B, respectively. Flexible outlet tubes (not shown) are coupled to the flow restricting components 60A, 60B to deliver medication to the sites, as needed.

In one aspect of the present invention, the inner diameter of the flow restricting components 60A, 60B are relatively small, e.g., 0.001 to 0.002 inches and a small manufacturing tolerance. The flow restricting components 60A, 60B are dimensioned to provide a large resistance to the flow of medication relative to resistance provided by the flexible outlet tubes and the sites where the medication is delivered. This assists in controlling the back pressure and thus minimizing the risk of uneven back pressure causing an unequal amount of medication to be delivered to the two sites.

In another aspect of the present invention, the flexible diaphragm 36 includes an integrally molded O-ring 62 around its outer perimeter 64. The O-ring 62 is press fit within a circular groove 66 in the valve housing 16. The valve housing 16 includes one or more air release apertures 68 which allow air to escape the groove 66 as the O-ring 62 is pressed into the groove 66. The O-ring 62 and the groove 66 ensures that the outer perimeter 64 is coupled to the valve housing, thereby forming the pressure chamber 22.

Figure 1:
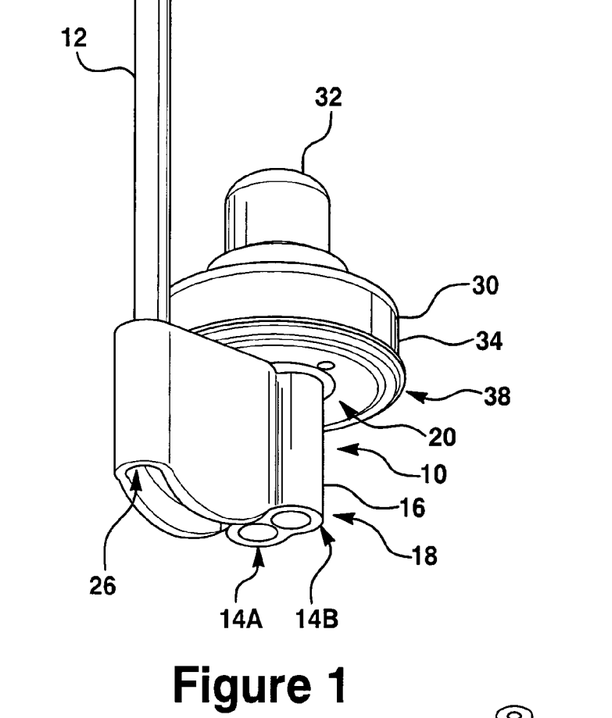
FIG. 1 is a first isometric view of a two site infusion apparatus, according to an embodiment of the present invention.
Figure 2:
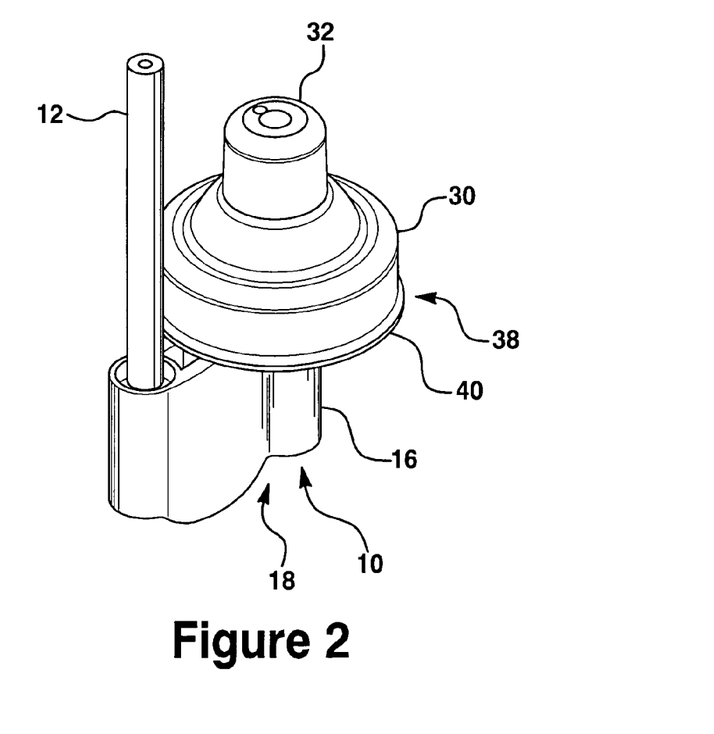
FIG. 2 is a second isometric view of the two site infusion apparatus of FIG. 1.
Figure 3:
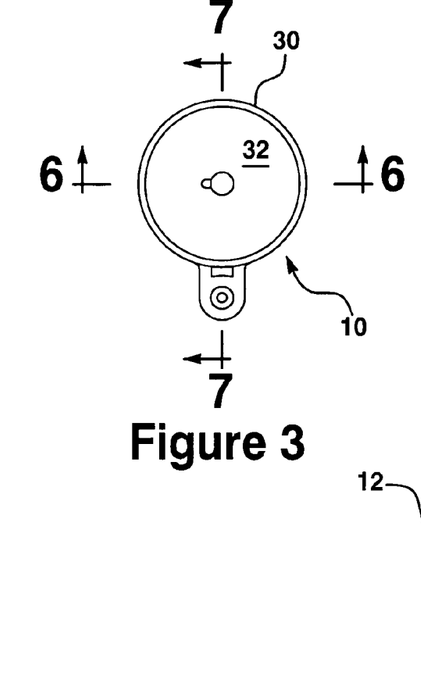
FIG. 3 is a top down view of the two site infusion apparatus of FIG. 1.
Figure 4:
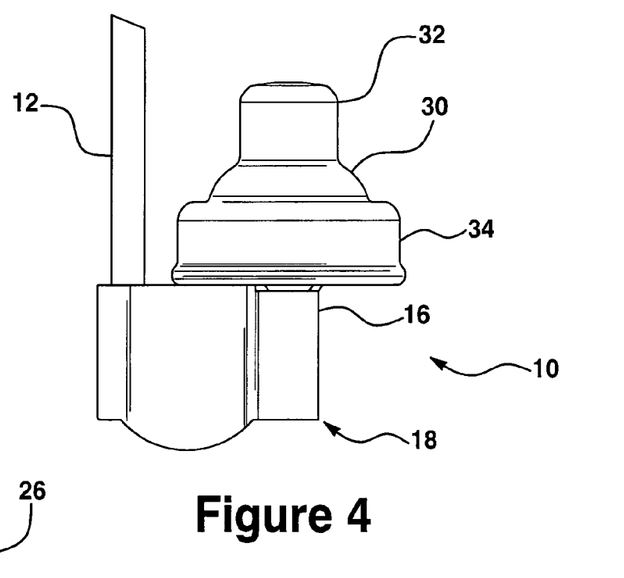
FIG. 4 is a side view of the two site infusion apparatus of FIG. 1.
Figure 5:
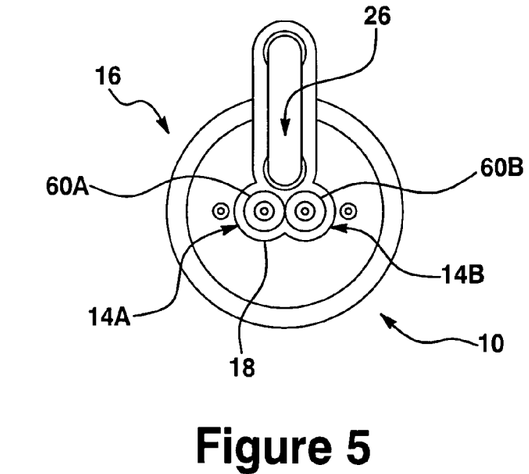
FIG. 5 is a bottom view of the two site infusion apparatus of FIG. 1.
Figure 6:
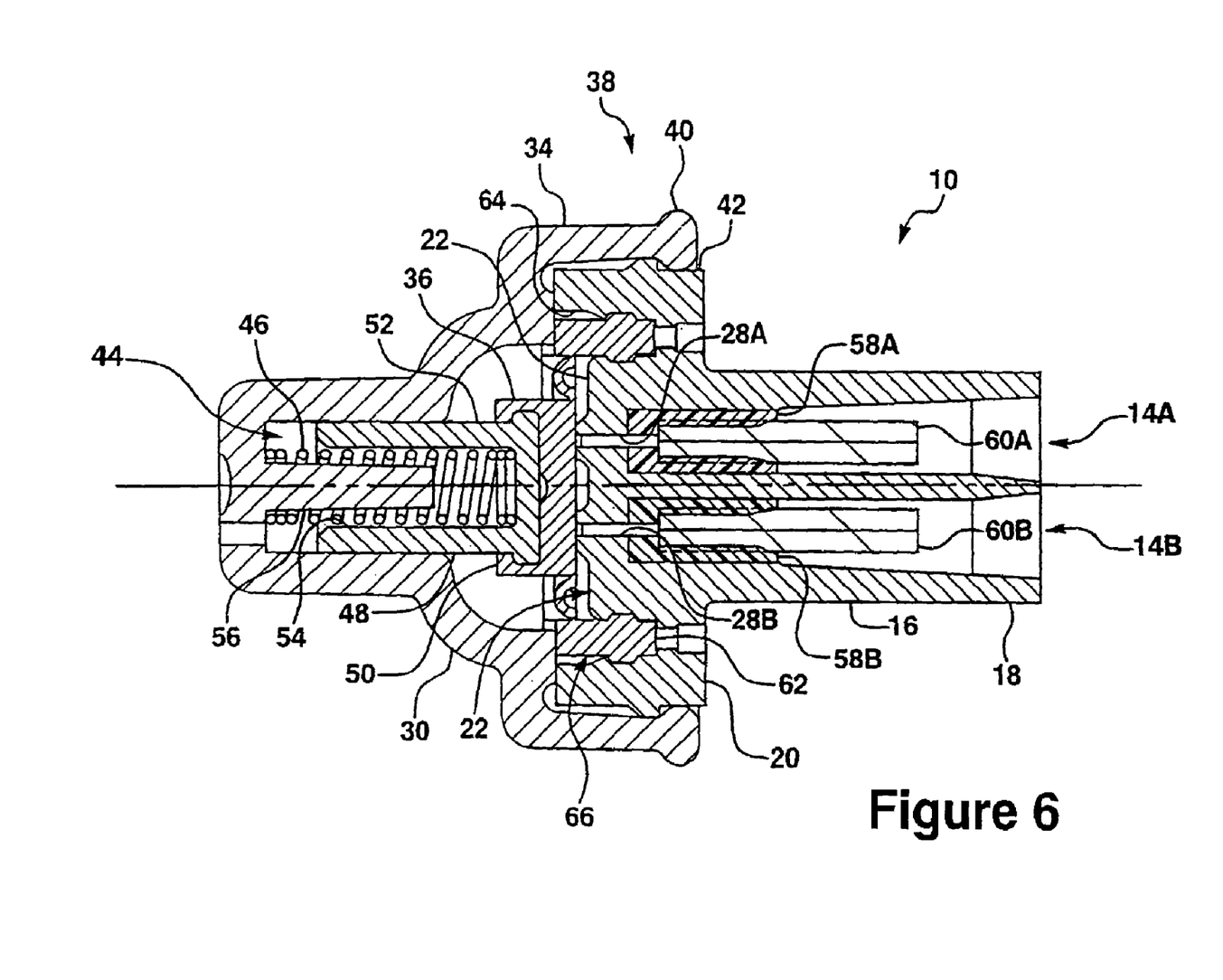
FIG. 6 is a first cut-away view of the two site infusion apparatus of FIG. 1.
Figure 7:
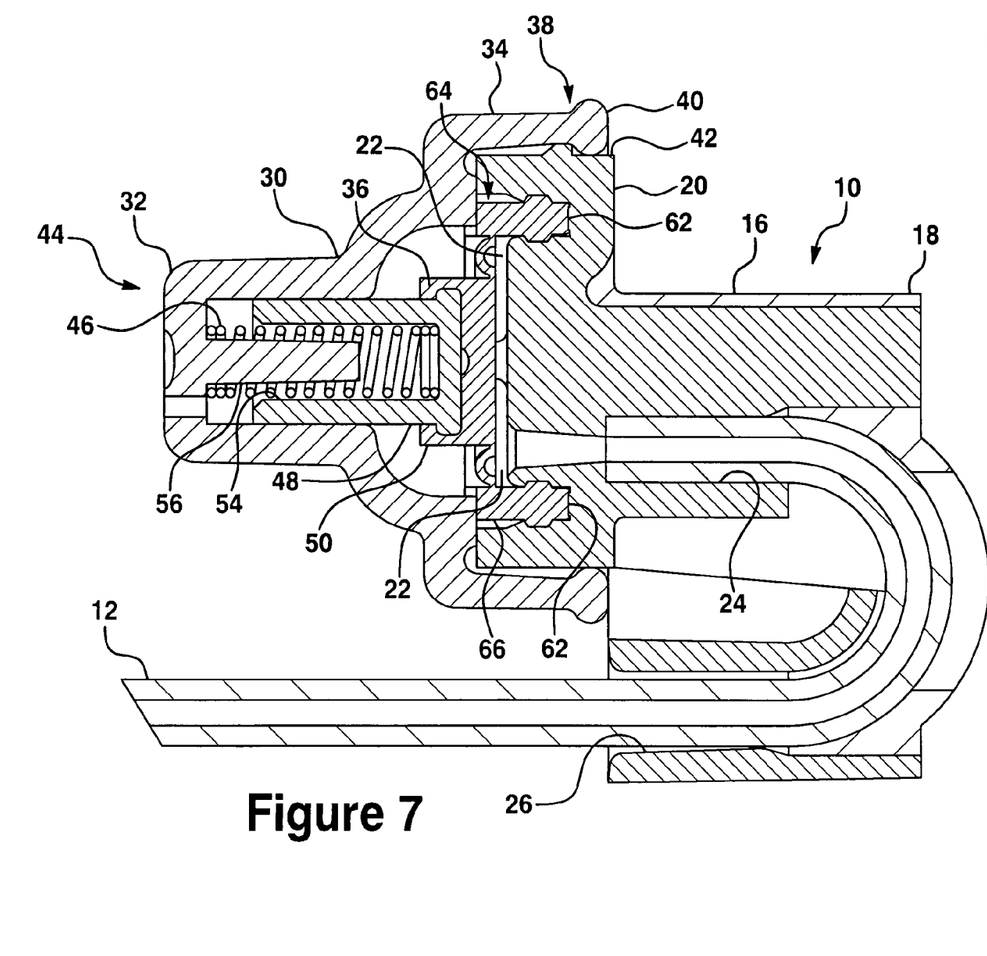
FIG. 7 is s second cut-away view of the two site infusion apparatus of FIG. 1.
Figure 8:
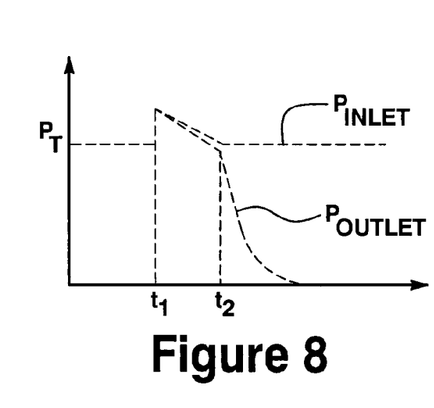
FIG. 8 is a graph illustrating operating parameters of the present invention.
Figure 9:
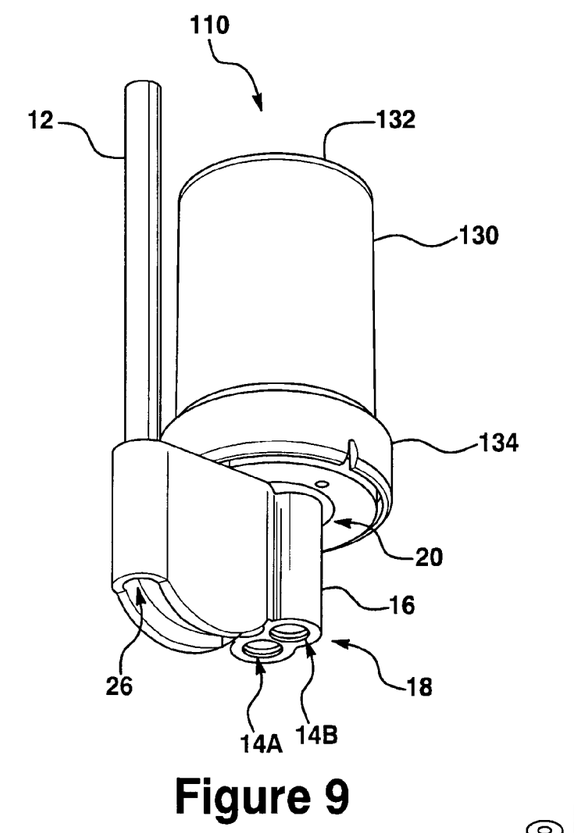
FIG. 9 is a first isometric view of a two site infusion apparatus, according to a second embodiment of the present invention.
Figure 10:
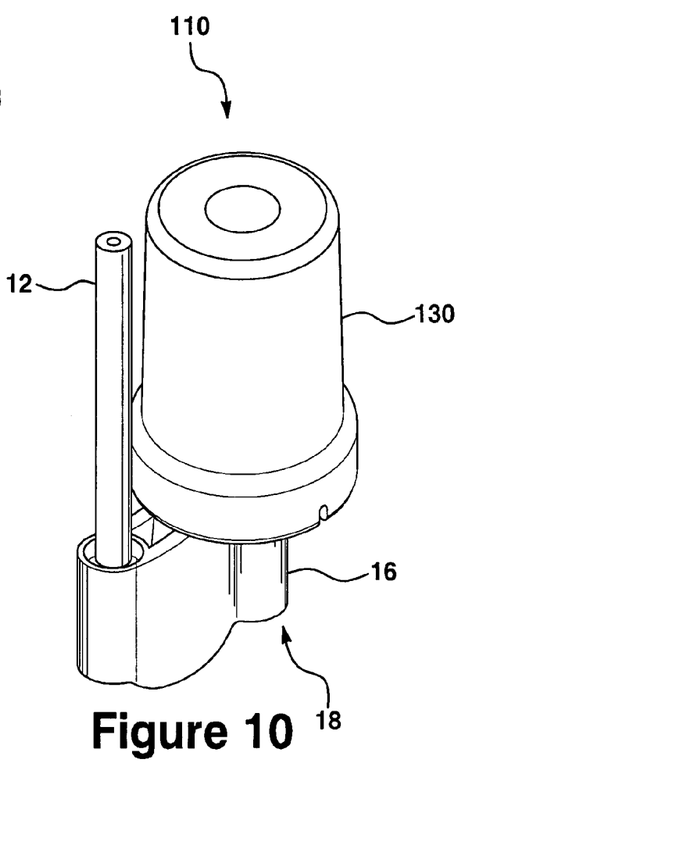
FIG. 10 is a second isometric view of the two site infusion apparatus of FIG. 9.
Figure 11:
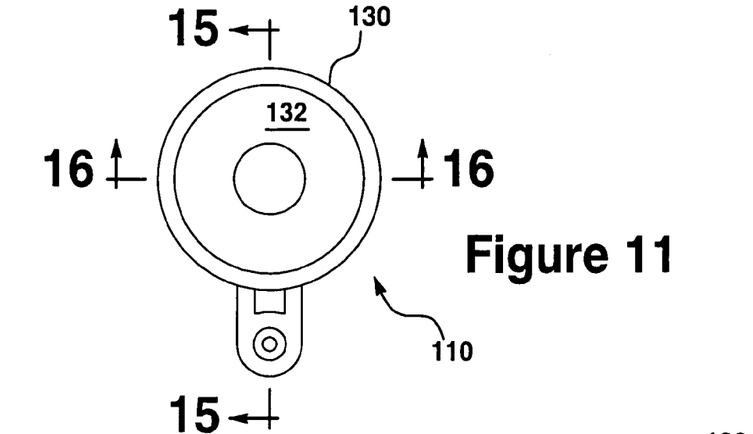
FIG. 11 is a top down view of the two site infusion apparatus of FIG. 9.
Figure 12:
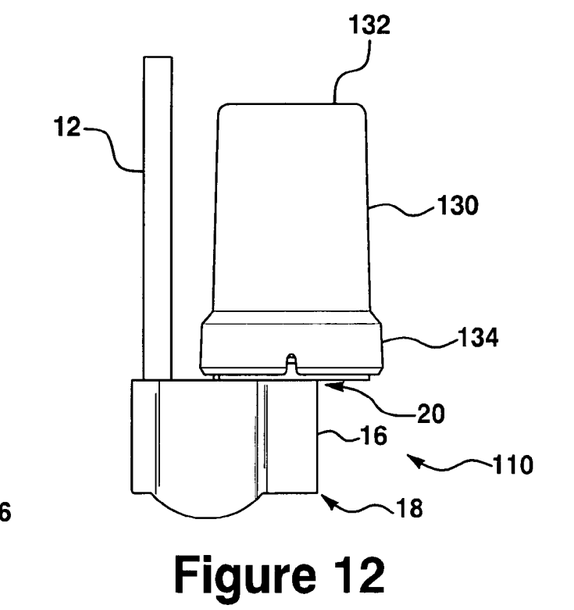
FIG. 12 is a side view of the two site infusion apparatus of FIG. 9.
Figure 13:
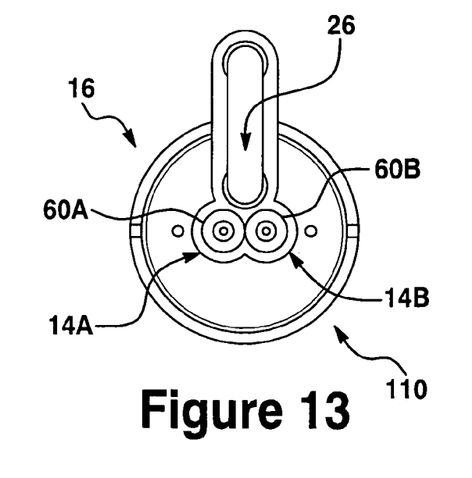
FIG. 13 is a bottom view of the two site infusion apparatus of FIG. 9.
Figure 14:
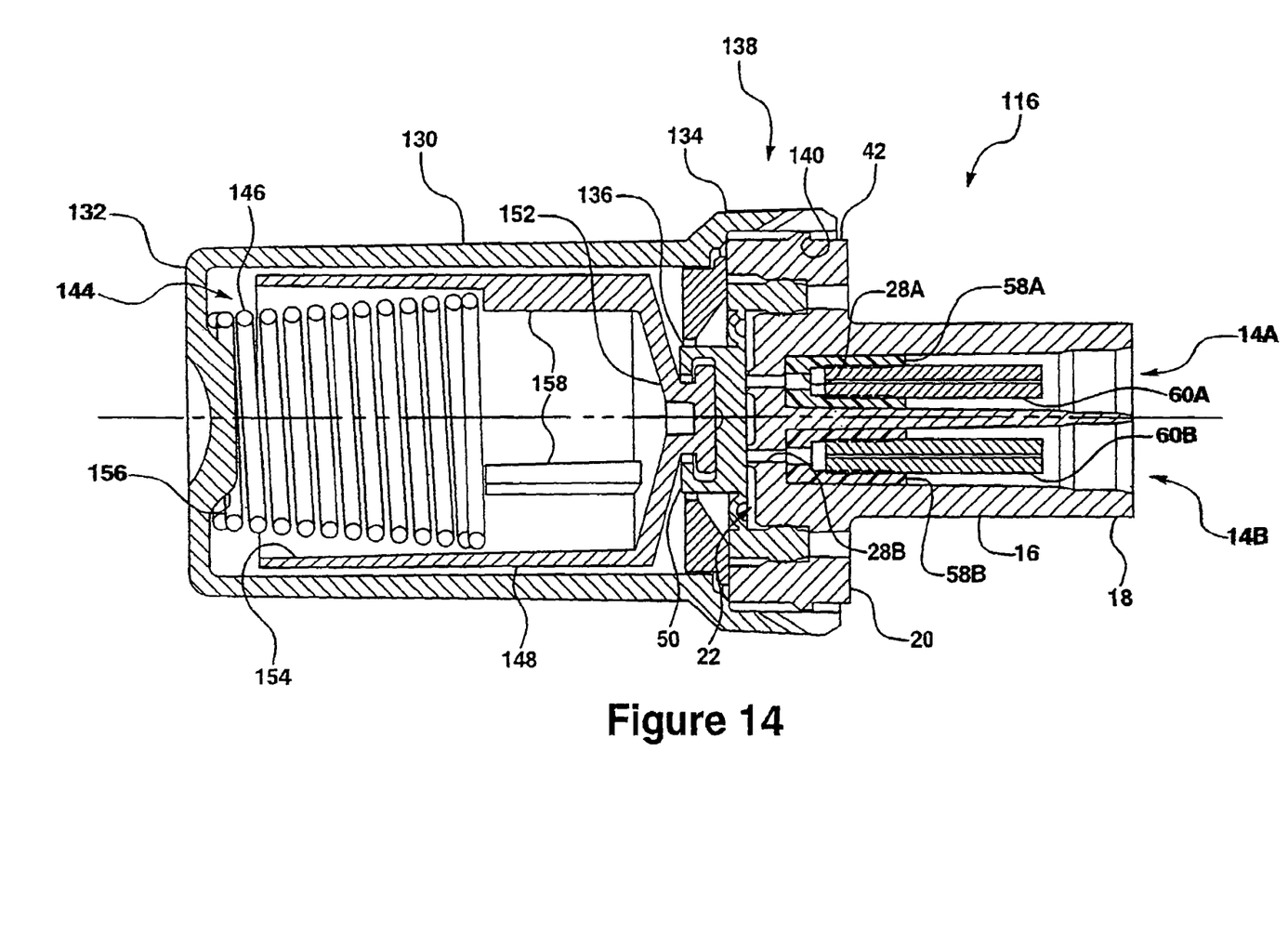
FIG. 14 is a first cut-away view of the two site infusion apparatus of FIG. 9.
Figure 15:
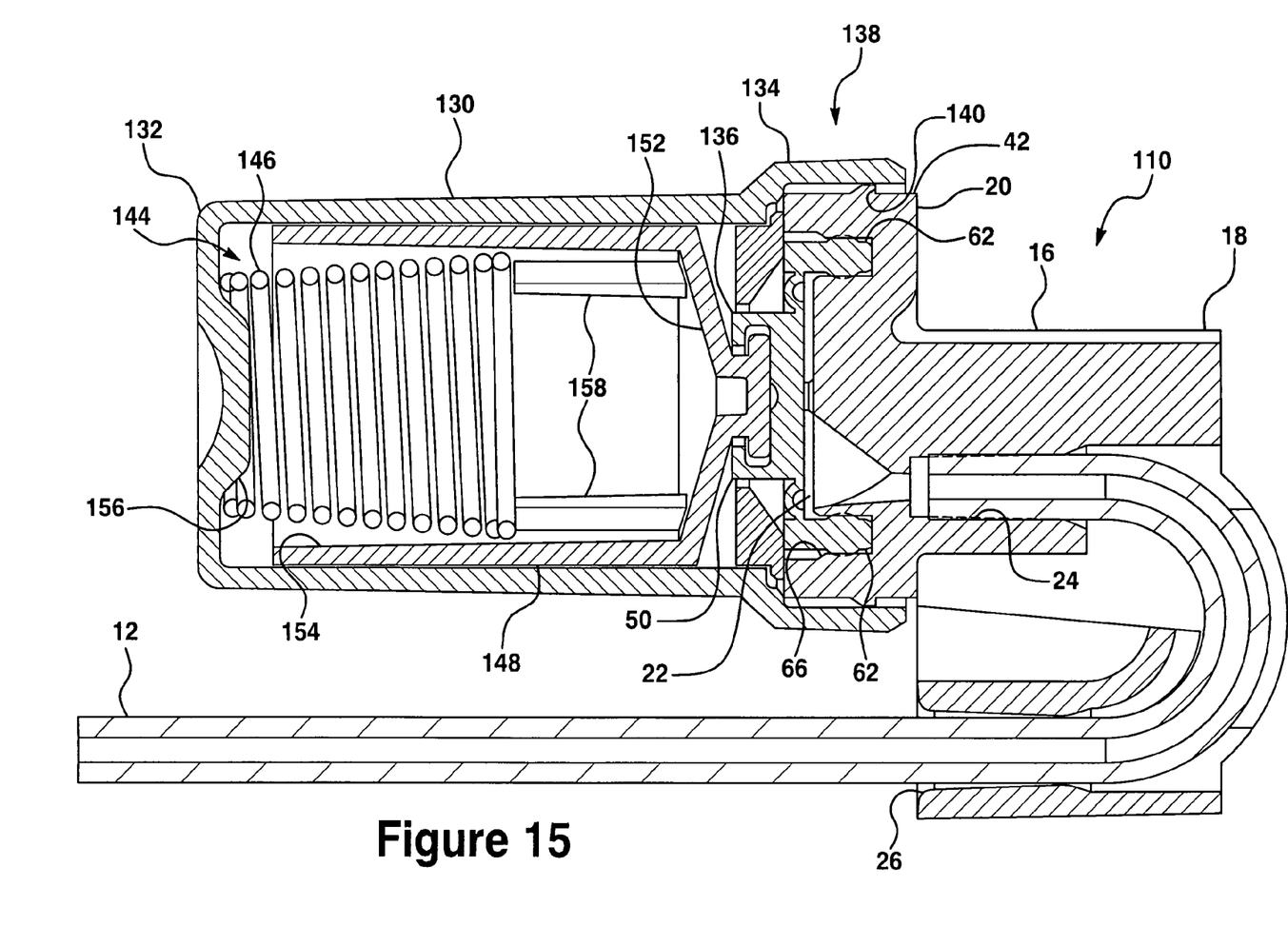
FIG. 15 is s second cut-away view of the two site infusion apparatus of FIG. 9.

In operation, the medication delivery system delivers medication through the inlet tube 12 in pulses. With reference to FIG. 8, when the flexible diaphragm 36 is in the closed position, the flexible diaphragm 36 creates a seal on the outlet valve seats. As fluid is pumped in, a pressure is created ($P_{inlet}$) within the pressure chamber 22. With the flexible diaphragm 36 in the closed position, no flow of medication is allowed from the pressure chamber 22 to the output orifice 14A, 14B. Thus, while the flexible diaphragm 36 is in the closed position, the pressure at the outlet orifices 14A, 14B ($P_{outlet}$) is substantially zero.

When the "pulse" of medication from the medication delivery system begins, $P_{inlet}$ quickly ramps up from a non-zero value. When the force exerted by the pressurized medication within the pressure chamber 22 on the flexible diaphragm 36 is great enough to overcome the force exerted by the biasing mechanism 44 ($P_T$), the flexible diaphragm 36 is moved from the closed position towards the open position ($t_1$). After the flexible diaphragm 36 is moved away from the closed position, fluid flows out of the valve and ramps down towards a non-zero value until the force exerted by the biasing mechanism 44 overcomes the force exerted on the flexible diaphragm by the medication within the pressure chamber 22 ($t_2$). The rate of fluid flow and therefore pressure decrease is controlled by the flow restricting components 60A, 60B. This control is important since too low of a restriction would not force a complete opening of the valve. In that case the restriction of flow across the valve seats would be significant and minor variations in manufacturing tolerances and/or finishes would control the flow resistance and resultant distribution. With proper flow restrictor selection, the apparatus 10 fully opens and this does not occur.

Likewise, when the flexible diaphragm 36 is moved away from the closed position, Poutlet quickly ramps up to a pressure substantially equal to or slightly less than Pinlet. While the flexible diaphragm 36 is open, $P_{inlet}$ tracks $P_{outlet}$. Since the resistance seen at the first and second orifices 14A, 14B is a result of the resistance of the first and second flow restricting components 60A, 60B, $P_{outlet}$ at the first and second orifices 14A, 14B are substantially equal. Once the flexible diaphragm 36 closes, $P_{outlet}$ quickly drops back down to substantially zero.

$$V_T = \int_{T_D}^{T_F} \dot{V}_T \, dt$$

Since $\dot{V} = \dot{V}_A + \dot{V}_B$, and $V_T = V_A + V_B$ then, $$V_A = \int_{T_D}^{T_F} \dot{V}_A \, dt$$

$$V_B = \int_{T_D}^{T_F} \dot{V}_B \, dt$$

But we know that $$\dot{V} = \frac{\Delta P}{R_T} = \frac{P_{outlet} - P_B}{R_T}$$

$$\therefore V_A = \int_{T_D}^{T_F} \frac{P_{outlet} - P_{DA}}{R_A + R_{DA}} \, dt$$

and $$V_B = \int_{T_D}^{T_F} \frac{P_{outlet} - P_{DB}}{R_B + R_{DB}} \, dt$$

Thus, if $P_{outlet} >> |P_{DA} - P_{DB}|$ and $R >> R_D$ and $R_A \approx R_B$ then, $V_A \approx V_B$ (Approximately Equal Flow)

With reference to FIGS. 9-15, a two site infusion apparatus 110 according to another embodiment of the invention is shown. In FIGS. 9-15, similar parts are labeled the same as in the previous Figures.

In the second embodiment, an end cap 130, with a generally cylindrical shape, has a closed end 132 and an open end 134. The end cap 130 is removably coupled to the valve housing 16 at the open end 134. For example, the end cap 130 may be bonded to the valve housing 16 by an adhesive. In one aspect of the invention, gaps in the adhesive bonding the end cap 130 to the valve housing 16 allow air to escape. The flexible diaphragm 36 is coupled between the end cap 130 and the valve housing 16 and is movable from a closed position to an open position, as described above.

As shown, the open end 134 of the cap 130 has an outer perimeter 138. The outer perimeter 138 includes an internal flange 140 which mates with the detent 42 on the valve housing 16 which allows the valve housing 16 and the end cap 130 to be removably snapped together.

The apparatus 110 includes a biasing mechanism 144 coupled between the cap 130 and the flexible diaphragm 36 for biasing the flexible diaphragm 36 towards the closed position. In one embodiment of the present invention, the biasing mechanism 144 includes a biasing spring 146 with a generally conical shape.

A piston 148 is juxtaposed between the biasing spring 146 and the flexible diaphragm 136. The piston receiving aperture 50 receives a first end 152 of the piston 148.

The piston 148 is hollow and includes a spring receiving chamber 154. The end cap 130 includes a spring positioning member 156. One end of the spring 146 is seated against seatings 158 within the spring receiving chamber 154 and the other end is centered on the spring positioning member 156.

Figure 16:
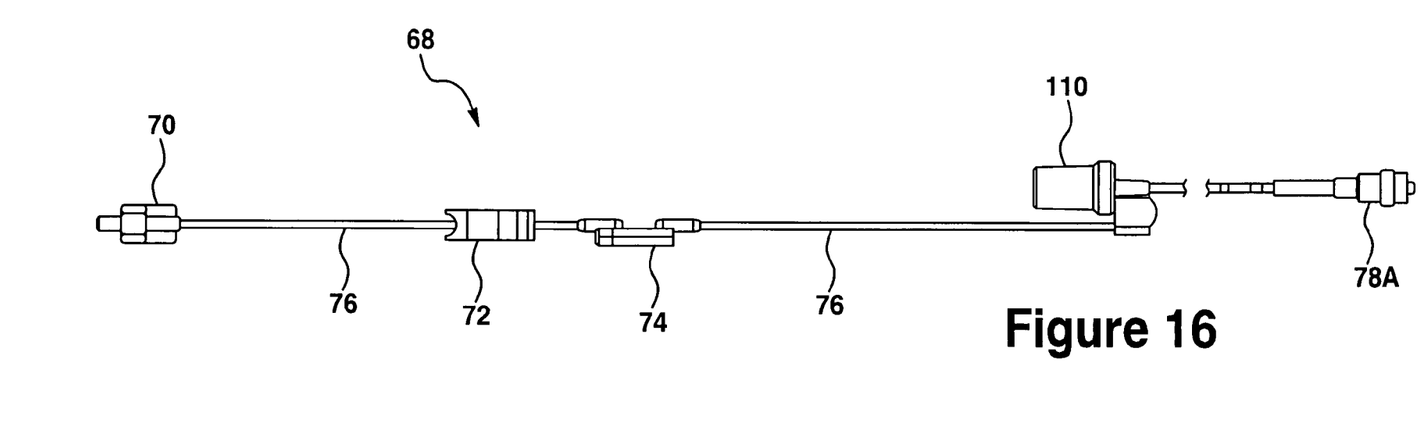
FIG. 16 is an diagrammatical illustration of a tube set including the two site infusion apparatus of FIG. 9; and, FIG. 17 is a second diagrammatical illustration of the tube set of FIG. 16.
Figure 17:
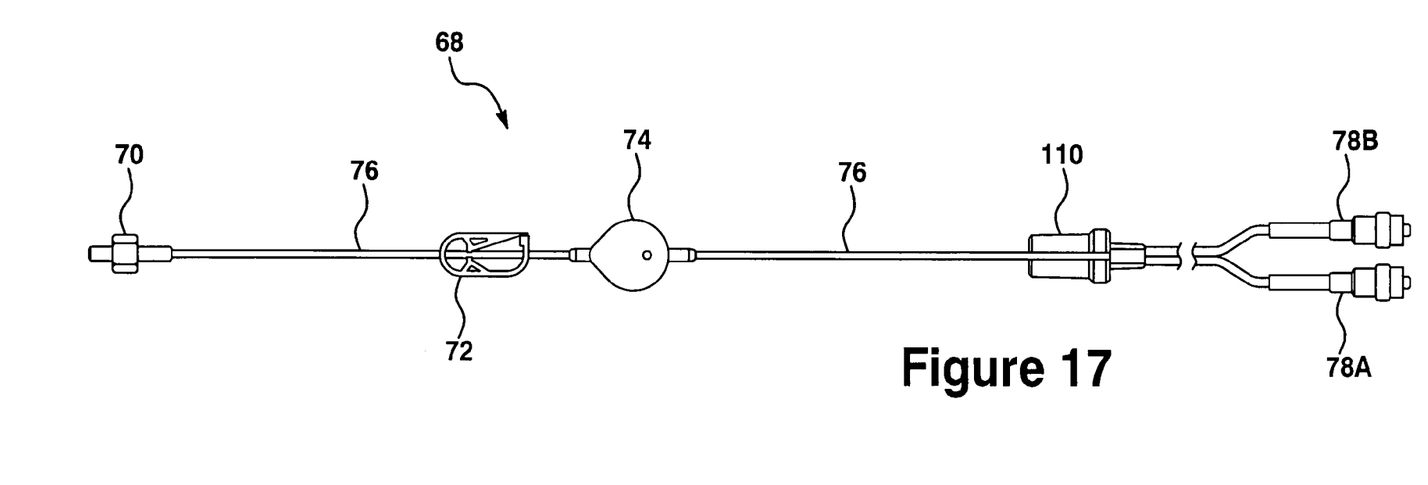

With reference to FIGS. 16-18, an exemplary tube set 68 including the two site infusion apparatus 110 of the second embodiment is shown. The tube set 68 maybe used with a delivery system (not shown). A suitable delivery system is disclosed in U.S. patent application Ser. No. 10/461,939, filed Jun. 13, 2003, which is hereby incorporated by reference.

The infusion tube set 68 includes a first connector 70 for connection to the delivery system, an on/off clamp 72 and an inline filter 74. Tubing 76 couples the connector 70 with the inline filter 74 and the inline filter 74 with the two site infusion apparatus 110. Tubing 76 also connects the first and second flow restricting components 60A, 60B to second and third connectors 78A, 78B.

Other aspects and features of the present invention can be obtained from a study of the drawings, the disclosure, and the appended claims.

ELEMENT LIST 10 two site infusion apparatus
12 medication delivery system output tube or inlet tube
14A first outlet orifice
14B second outlet orifice
16 valve housing
18 first end of valve housing
20 second end of valve housing
22 pressure chamber
24 inlet orifice
26 inlet passage
28A first outlet passage
28B second outlet passage
30 end cap
32 closed end
34 open end
36 flexible diaphragm
38 outer perimeter
40 ridge
42 detent
44 biasing mechanism
46 biasing spring
48 piston
50 piston receiving aperture
52 first end of the piston
54 spring receiving chamber
56 spring positioning pin
58A first bushing
58B second bushing
60A first glass tube
60B second flow restriction components
62 integral O-ring
64 outer perimeter of flexible diaphragm
66 groove
68 tube set
70 first connector
72 on/off clamp
74 inline filter
76 tubing
78A second connector
78B third connector
110 two site infusion apparatus
130 end cap
132 closed end
134 open end
138 outer perimeter
50 140 internal flange
154 spring receiving chamber
156 spring positioning member
158 seatings

What is claimed is:

1. An apparatus for use in delivering medication to separate locations from a single source of medication, comprising:
a valve housing defining an inlet for receiving the medication from the single source of medication and defining first and second outlets of substantially equal flow capacity for delivering the medication to the separate locations in substantially equal amounts, said valve housing having a longitudinal axis and said outlets being spaced from and parallel to said longitudinal axis;
a cap having an open end coupled to said valve housing;
a flexible diaphragm disposed between said cap and said valve housing to define a pressure chamber in fluid communication with said inlet and said outlets, said flexible diaphragm movable between a closed position to seal said pressure chamber from said outlets and an open position to open said pressure chamber to said outlets;
a biasing mechanism operable between said cap and said flexible diaphragm for biasing said flexible diaphragm towards said closed position, said biasing mechanism being disposed about said longitudinal axis;
a pair of flexible tubes elongated between proximal and distal ends, each of said proximal ends coupled to one of said outlets for conveying the medication from said outlets to the separate locations; and
a pair of connectors, each of said connectors coupled to one of said flexible tubes at said distal ends thereof.

2. An apparatus as set forth in claim 1 wherein said biasing mechanism includes a piston disposed in said cap for providing axial alignment and a spring disposed between said cap and said piston.

3. An apparatus as set forth in claim 2 wherein said flexible diaphragm includes a head portion and said piston has a first end coupled to said head portion for moving with said head portion as said flexible diaphragm moves between said closed and open positions.

4. An apparatus as set forth in claim 2 wherein said piston includes a bottom and a peripheral wall extending from said bottom to define a spring chamber, said spring being disposed in said spring chamber.

5. An apparatus as set forth in claim 4 wherein said spring has a first end disposed in said spring chamber and a second end engaging said cap, said spring having an outside dimension that decreases from said first end to said second end for minimizing frictional contact between said spring and said peripheral wall or between coils of said spring and said peripheral wall.

6. An apparatus as set forth in claim 5 wherein said spring has a generally frustoconical shape.

7. An apparatus as set forth in claim 4 wherein said piston includes a plurality of spring seats disposed on said peripheral wall inside said spring chamber, said spring seats being circumferentially spaced along said peripheral wall for engaging said spring.

8. An apparatus as set forth in claim 7 wherein said cap has a closed end, opposite said open end, and a spring positioning member disposed on said closed end and extending inwardly toward said open end, said spring being centered on said spring positioning member.

9. An apparatus as set forth in claim 1 including a first bushing disposed in said first outlet and a second bushing disposed in said second outlet.

10. An apparatus as set forth in claim 9 including a first flow restricting component disposed within said first bushing and a second flow restricting component disposed within said second bushing.

11. An apparatus for use in delivering medication to separate locations from a single source of medication, comprising:
- a valve housing defining an inlet for receiving the medication from the single source of medication and defining first and second outlets of substantially equal flow capacity for delivering the medication to the separate locations in substantially equal amounts, said valve housing having a longitudinal axis and said outlets being spaced from and parallel to said longitudinal axis;
- a cap having an open end coupled to said valve housing;
- a flexible diaphragm disposed between said cap and said valve housing to define a pressure chamber in fluid communication with said inlet and said outlets, said flexible diaphragm movable between a closed position to seal said pressure chamber from said outlets and an open position to open said pressure chamber to said outlets;
- a control block disposed between said flexible diaphragm and said cap, said control block having a control surface disposed about said longitudinal axis for receiving said flexible diaphragm as said flexible diaphragm moves from said closed position to said open position to provide controlled movement of said flexible diaphragm from said closed position to said open position;
- a pair of flexible tubes elongated between proximal and distal ends, each of said proximal ends coupled to one of said outlets for conveying the medication from said outlets to the separate locations; and
- a pair of connectors, each of said connectors coupled to one of said flexible tubes at said distal ends thereof.

12. An apparatus as set forth in claim 11 wherein said control block has a first end facing said flexible diaphragm and a second end, opposite said first end, facing said cap, said control surface defining a bore of said control block that tapers from said first end toward said second end.

13. An apparatus as set forth in claim 12 wherein said flexible diaphragm has a seat portion fixed relative to said valve housing, a head portion movable in said tapered bore between said closed and open positions, and a connecting portion flexibly connecting said seat portion and said head portion, said connecting portion contacting said control surface in said tapered bore as said flexible diaphragm moves from said closed position to said open position.

14. An apparatus as set forth in claim 11 including a biasing mechanism disposed between said cap and said flexible diaphragm for biasing said flexible diaphragm towards said closed position.

15. An apparatus as set forth in claim 14 wherein said biasing mechanism includes a piston disposed in said cap for providing axial alignment and a spring disposed between said cap and said piston.

16. An apparatus as set forth in claim 15 wherein said flexible diaphragm includes a head portion and said piston has a first end coupled to said head portion for moving with said head portion as said flexible diaphragm moves between said closed and open positions.

17. An apparatus as set forth in claim 15 wherein said piston includes a bottom and a peripheral wall extending from said bottom to define a spring chamber, said spring being disposed in said spring chamber.

18. An apparatus as set forth in claim 17 wherein said spring has a first end disposed in said spring chamber and a second end engaging said cap, said spring having an outside dimension that decreases from said first end to said second end for minimizing frictional contact between said spring and said peripheral wall or between coils of said spring and said peripheral wall.

19. An apparatus as set forth in claim 18 wherein said spring has a generally frustoconical shape.

20. An apparatus as set forth in claim 17 wherein said piston includes a plurality of spring seats disposed on said peripheral wall inside said spring chamber, said spring seats being circumferentially spaced along said peripheral wall for engaging said spring.

21. An apparatus as set forth in claim 20 wherein said cap has a closed end, opposite said open end, and a spring positioning member disposed on said closed end and extending inwardly toward said open end, said spring being centered on said spring positioning member.

22. An apparatus as set forth in claim 11 including a first bushing disposed in said first outlet and a second bushing disposed in said second outlet.

23. An apparatus as set forth in claim 22 including a first flow restricting component disposed within said first bushing and a second flow restricting component disposed within said second bushing.

* * * * *